United States Patent [19]
Sick

[11] 4,181,398
[45] Jan. 1, 1980

[54] OPTICAL APPARATUS

[75] Inventor: Erwin Sick, Icking, Fed. Rep. of Germany

[73] Assignee: Erwin Sick Gesellschaft mit beschrankter Haftung Optik-Elektronik, Waldkirch, Fed. Rep. of Germany

[21] Appl. No.: 853,890

[22] Filed: Nov. 22, 1977

[30] Foreign Application Priority Data

Dec. 1, 1976 [DE] Fed. Rep. of Germany ....... 2654465

[51] Int. Cl.² .......................... G02B 5/14; G01J 1/42
[52] U.S. Cl. ................. 350/96.10; 356/222; 356/225; 250/227
[58] Field of Search ............. 350/96.10, 96.28; 250/227; 362/32; 356/222, 225

[56] References Cited

U.S. PATENT DOCUMENTS

| | | | |
|---|---|---|---|
| 2,945,958 | 7/1960 | Morris | 350/96.1 |
| 3,317,738 | 5/1967 | Piepenbrink et al. | 250/227 |
| 3,728,548 | 4/1973 | Pinior | 350/96.10 |
| 4,085,322 | 4/1978 | Sick | 250/227 |

FOREIGN PATENT DOCUMENTS

1,240,674 5/1967 Fed. Rep. of Germany ........ 350/96.10
1363539 5/1964 France ........................ 350/96.10

OTHER PUBLICATIONS

M. M. Chen et al., "The Use of a Kaleidoscope to Obtain Uniform Flux . . . " Applied Optics, vol. 2, No. 3, Mar. 1963, pp. 265-271.

L. B. Richards, "Photodetector As Function Detector," IBM Tech Disclosure Bulletin, vol. 13, No. 3, Aug. 1970, pp. 591-592.

*Primary Examiner*—Rolf G. Hille

[57] ABSTRACT

A light smoothing device for rendering a non uniform distribution of light more uniform especially suited for use in line scanning in combination with a light conducting rod which transmits light incident on its surface to its end faces for subsequent detection. The smoothing device has an optical passage with a reflecting interior surface an inlet to the passage and a detector at the other end of the passage. The passage ensures at least part of the light entering the inlet is reflected prior to incidence on the detector.

A number of forms of optical passage are disclosed having various reflecting segments of convex, plain or concave curvature.

12 Claims, 6 Drawing Figures

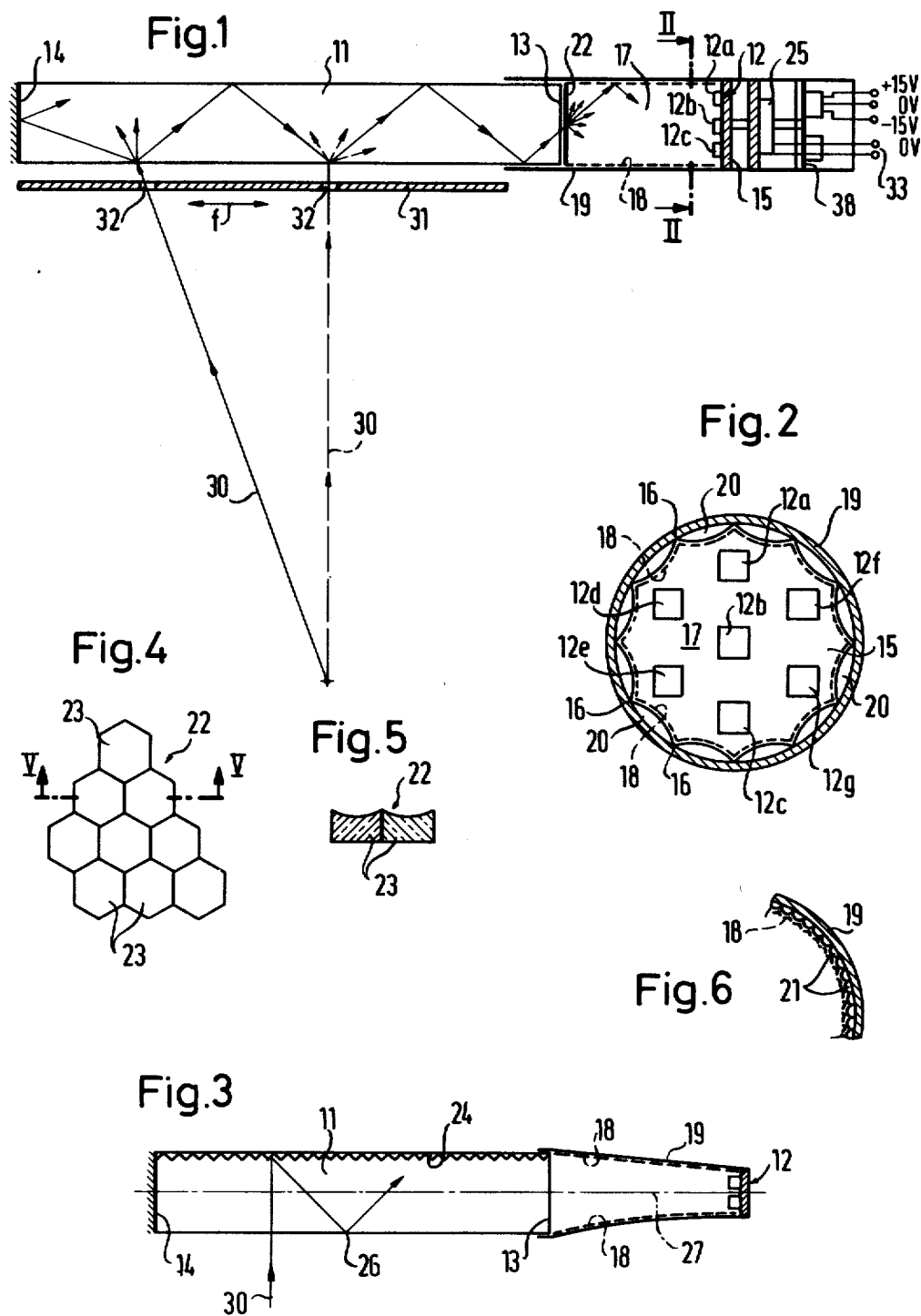

OPTICAL APPARATUS

The present invention relates to improvements in optical apparatus and has particular reference to an optical device arranged at one end of light conducting rod whereby light incident on the periphery of the rod and conducted by total reflection to an end face of the rod is smoothed by the optical device from a non-uniform distribution of light to a more uniform distribution prior to impingement on a light receiving device.

Such a device is useful for the comparative measurement of light radiation received by the light conducting rod and detected by the light receiving device which subsequently generates an output signal proportional to the light radiation received.

With known light conducting rods there is disposed at the relevant end face of the rod a light receiving device, preferably a photoelectric multiplier tube which however receives light which is distributed with very uneven intensity over the input screen.

In as much as the beam of light incident on the light conducting rod scans along the surface of the light conducting rod the pattern of light received is continually changing.

This can lead to variations in the output signal from the light receiving device even when the incident ray on the sheath of the light conducting rod is of constant intensity.

Light scattering elements such as a ground glass or opaline glass screen disposed between the end face of the light conducting rod and the light receiving device can result in a desired smoothing of the received light but result in losses of light that are not acceptable especially where other converters for light to electricity, such as photodiodes, are used in place of the very sensitive and in many respects disadvantageous photoelectric multipliers.

The present invention seeks to provide an optical device of the aforementioned kind which makes possible the effective comparative measurement of light leaving the light conducting rod without significant loss of intensity.

According to the present invention there is provided optical apparatus comprising an optical passage having an inlet for light at one end, a reflecting surface for reflecting light internally of the passage and a light receiving device at the other end whereby at least a part of the light entering the said inlet is reflected by the reflecting internal surface prior to impinging on the light receiving device.

Preferably the inlet to the optical passage communicates with one end face of a light conducting rod and the light receiving device comprises a photoelectric detector.

Because of the reflecting internal surface of the passage, all the light leaving the light conducting rod is passed to the photoelectric detector, apart that is from the trivial amount of light lost on reflection; this results in a high working efficiency.

The reflection, at least once, of the larger part of the available light produces a mixing or smoothing of the light rays so that an essentially regular distribution of light intensity is perceived at the light receiving device. This smoothing effect is further improved by ensuring that at least a part of the available light from the light conducting rod is multiply reflected to and fro on the reflecting internal surface of the optical passage.

In a preferred embodiment the optical passage senses at its end which mates with the end face of the light conducting rod at least the entire surface of the rear end of the light conducting rod. This ensures that all the light available from the rear end of the light conducting rod enters the optical passage. In the interest of producing a compact unitary arrangement it is especially useful for the respective end of the optical passage to encircle the rear end of the light conducting rod.

The optical passage is preferably defined by a hollow body having an internal surface which is made to be reflecting. This can take the form of a stiff reflecting foil that is formed by rolling it into a hollow essentially cylindrical body open at both ends.

It is however also possible for the optical passage to be constructed in the form of a solid transparent body in which the reflecting internal surface is provided by applying the reflecting material to the outside of the body. The advantage of this construction is that it yields a very stable construction of the optical passage. This has the optical advantage that the light available from the rear end of the light conducting rod is not refracted away from the axis of the light conducting rod so that a steeper incidence of the light at the photoelectric detector is made possible than when refraction of the light away from the axis is caused by the transition from glass to air. The construction of the optical passage in the form of a hollow body has however the advantage that, for the same length of passage, more reflections of the light are possible because the angle of incidence on the internal reflecting surface is steeper.

An especially favoured embodiment is characterised in that the reflecting periphery of the optical passage is divided into individual sections which have a curvature differing from that of the circular form of the light conducting rod.

Because of the curvature of the light conducting rod which, for manufacturing reasons, is generally cylindrical the light reflected on the inner wall is periodically concentrated into focal lines of approximately one quarter of the diameter of the rod.

These periodic concentrations would in a cylindrical optical passage repeat in approximately the diameter of the passage which would not be so useful for the purpose of smoothing out the light variations.

The deviation of the curvature of the individual sections should therefore be of such a size that the concentration effect does not effect, or only by a trivial amount, the photoelectric light detector. Breaks or apex lines exist between the individual sections of the periphery of the optical passage.

In an especially simple and practical embodiment the individual sections are made flat. The optical passage therefore comprises a plurality of elongate plain mirrors arranged into a cylinder with breaks or apex lines between the individual mirrors.

It is of especial advantage for the smoothing of the light when the individual sections are formed with the opposite curvature to that of the light conducting rod. When seen overall the optical passage has a curvature approximately that of a cylinder in detail however the individual sections are oppositely curved to the cylinder, inbetween the individual sections are the breaks or apex lines.

A very simple method of manufacture for such hollow bodies comprises the periodic nicking of a pre-curved relatively stiff foil which is subsequently folded back on itself and formed into a hollow body. The individual sections thereby retain essentially their original curvature whilst a hollow body results which is curved in the opposite direction.

The oppositely curved individual sections result in the achievement of a light scattering effect which becomes more pronounced as the curvature of the individual sections is increased. The individual sections should however if possible not extend over more than a quarter of a cylinder in order that additional losses through reflection are not sustained.

Around the periphery of the hollow body there are preferably between six and eighteen such sections, twelve sections being suitable.

In one embodiment the optical passage is of cylindrical shape which befits it for operation with a photoelectric detector in the form of a diode array or a photoelectric multiplier.

The optical passage can also taper away from the light conducting rod and be of generally conical form. The wall of the optical passage can also taper in accordance with an exponential curve. These embodiments are useful when the light receiving device has a smaller surface area than the rear end of the light conducting rod. By this means the light is concentrated onto the light receiving device.

A further simple and economically producable embodiment that is simultaneously of high efficiency is characterised by an optical passage constructed of a coiled screen of cylindrical lenses whose cylindrical lenses are provided with reflecting surfaces and disposed towards the interior of the passage. The cylindrical lenses extend therefore generally parallel to the axis of the light conducting rod. This arrangement can likewise be constructed in the form of a truncated cone. Screens of cylindrical lenses are commercially available and solely require the provision of a reflecting surface and coiling to be put into a form useful for the present invention. The coiling is expediently achieved into the shape of a cylinder or a truncated cone.

At the inlet to the optical passage there is preferably arranged in addition a screen of individual lenses or two crossed screens of cylindrical lenses. The light leaving the light conducting rod is in this way already considerably scattered prior to impingement on the interior reflecting surface of the optical passage and indeed without considerable loss of light as occurs with a ground glass or opaline glass screen.

The simple disposition of an array of individual lenses between the rear end of the light conducting rod and the light receiving device would not suffice for achieving a sufficient smoothing of the light. In combination with optical passages suitable for the present invention however a completely satisfactory smoothing is achieved indeed even if the interior reflecting surface of the optical passage is constructed as a simple right cylindrical surface.

In the case in which a screen of individual lenses is used the loss of light is further reduced when the individual lenses are divergent lenses of hexagonal section. In this case there are no spaces between individual lenses which can give rise to light loss.

It should also be mentioned that the light smoothing device can be used anywhere where light rays leave a particular surface in varying directions and with varying intensities. E.g. the optical apparatus in accordance with the present reading can be used for smoothing the light emitted by the filament of an incandescent bulb. Particularly, by use of the tapering optical passage an evenly illuminating light spot is achieved that is suitable as a light source for optical apparatus in which a light source is required having an exceptionally regular intensity.

The light source which is emitting the irregular light rays, e.g. the incandescent bulb is to be thought of as positioned in place of the end face of the previously mentioned light conducting rod.

The light smoothing devices can be used with especial advantage in the light detection device disclosed and claimed in the simultaneously filed patent application of the present applicant entitled "Improvements in photoelectric light detection devices."

Embodiments of the invention will now be described by way of example only and with reference to the accompanying drawing in which:

FIG. 1 shows a schematic section through a light smoothing device arranged at one end of a light conducting rod.

FIG. 2 is a section on the line II—II of FIG. 1.

FIG. 3 is a schematic longitudinal section similar to FIG. 1 through a further advantageous embodiment.

FIG. 4 is a plan view of a single lens screen used in accordance with the invention.

FIG. 5 is a schematic section on the line V—V of FIG. 4 and

FIG. 6 a partly cut away section of a hollow body provided with a reflecting screen of cylindrical lenses forming a light smoothing device in accordance with the invention.

In FIG. 1 there is shown in simplified form a band of material 31 which is capable of movement in a plane at right angles to the plane of the drawing. The band is scanned linewise in rapid succession in the direction of the double arrow F by a laser light beam 30.

Directly behind the band of material 31 is disposed, parallel to the scanning direction and to the material band 31, a light conducting 11 so that, for example, faults appearing as apertures 32 in the band allow light to fall at various positions on the surface of the light conducting rod 11. This light is passed by refraction and scattering to the inside of the light conducting rod and; as is schematically indicated by arrows, is totally reflected to the end faces 13, 14 of the light conducting rod. The end face 14 is provided with a reflecting surface so that light arriving there is reflected and finally after many internal reflections arrives likewise at the other end face 13.

In the vicinity of the end face 13 a hollow body 19 having an interior reflecting surface 18 is pushed into place on the light conducting rod. The hollow body 19 and its reflecting interior surface define an optical passage 17 that is sufficiently long so that at least a portion of the light transmitted from the rear side 13 is reflected at least once on the reflecting interior surface before it impinges on a photodiode array 12 that comprises an array of individual photodiodes 12a, b, c, d, e, f and g, etc. (See also FIG. 2).

The array of photodiodes is fastened to a plate 15 arranged in the tube 19. Also arranged in the tube is a current voltage transformer 25, and an amplifier 38. The measuring signal is obtained from output 33.

As can be seen from FIG. 2 the periphery of the optical passage 17, i.e. the reflecting interior surface of the hollow body 19 is divided into individual sections 20 which each have a curvature opposite to that of the hollow body. In this manner there are formed light scattering elements which extend in the axial direction which enables the desired smoothing of the light pattern to be achieved.

FIG. 2 shows the preferred arrangement of 12 such elements 20 which lies within the preferred range of 6 to 18 elements. The break lines or apex lines 16 between the individual sections extend essentially parallel to the axis of the device.

Various curvatures for the individual sections are useful in various circumstances in particular a radius in the range ½ to ¼ of the radius of the light conducting rod is generally useful.

FIG. 6 illustrates an embodiment in which the interior surface of the hollow tube comprises a screen 21 of cylindrical lenses that carry the reflecting interior surface 18. In principle this is a similar construction to the sections 20 of FIG. 2 except that the individual convex cylindrical lenses or mirrors are considerably smaller and more numerous. In this manner from 2,000 to 3,000 small cylindrical lenses can be arranged around the periphery of the hollow body 19. The preferred number disposed around the periphery is however in the range 12 to 50.

As illustrated in FIG. 1 a further screen of individual lenses 22 is positioned between the optical passage 17 and the end face 13.

The construction of this further screen can be understood from FIGS. 4 and 5. The further screen comprises mixture lenses 23 of hexagonal section which are constructed to be flat on one side but concave on the other so that the net result is a diverging lens 23.

A strong scattering of the light rays emerging from the rear side 13 of the screen is thus already achieved by the screen 22 of lenses 23 and this is done without loss of light. This is illustrated by the small arrows of FIG. 1. The loss of light from a lens screen is extremely low.

The light entering into the optical passage 17 is finally reflected inwardly by the reflecting interior surface 18 whereby a scattering of the light occurs in accordance with the curvature of the individual lengthwise extending cylindrical mirrors 20.

A sufficient smoothing of the light is however achieved solely by the division of the periphery of the hollow body into individual sections 20.

Finally the light falls on one of the photodiodes 12a through g, and the smoothing is sufficiently good that practically the same output signal is given by all the diodes.

FIG. 3 shows a similar embodiment in which however, on the internal surface of the light conducting rod opposite to the side of the light conducting rod from which the light beam 30 enters, there is provided a mirror 24 with a stepped sawtooth surface which extends along one of the generatrices of the right cylindrical light conducting rod 11. By this means the light entering the light conducting rod is reflected in the manner shown a typical ray 30. With this advantageous embodiment the light scattering shown in FIG. 1 at the entry to the light conducting rod is not present. Rather, the light entering is internally reflected inside the light conducting rod under a quantified angle so that the total reflection shown at 26 takes place.

In this way almost all the light entering the light conducting rod reaches the end face 13 of the light conducting rod.

In the embodiment of FIG. 3 the light smoothing device is shown as a hollow body 19 which tapers away from the end face 13 of the light conducting rod. Above the centreline 27 there is illustrated one embodiment in which the tapering follows the shape of a cone and underneath the centreline a second arrangement in which the tapering follows an exponential curve. Clearly this embodiment makes it possible to use a smaller number of photodiodes for the photoelectric detector 12. If necessary a single photoelectric detector will suffice.

I claim:

1. Optical apparatus comprising an optical passage having an inlet for light at one end for receiving light from a light conducting rod, a reflecting surface for reflecting light internally of the passage and a light receiving device at the other end, there being a screen of individual diverging lenses at said inlet to said optical passage.

2. Optical apparatus comprising an optical passage having an inlet for light at one end for receiving light from a light conducting rod of substantially circular form, a reflecting surface for reflecting light internally of the passage, and a light receiving device at the other end, said reflecting surface being divided into individual reflecting sections which have a curvature differing from that of the circular form of the light conducting rod, whereby at least a part of the light entering the said inlet is reflected by the reflecting internal surface prior to impinging on the light receiving device.

3. Apparatus according to claim 1 in which said light receiving device comprises a photoelectric detector.

4. Apparatus according to claim 1 in which the inlet to the optical passage is adapted to receive light from at least the whole end face of the light conducting rod.

5. Apparatus according to claim 4 in which the inlet to the optical passage surrounds the end face of the light conducting rod.

6. Apparatus according to claim 1 in which the optical passage is defined by a hollow body having a reflecting interior surface.

7. Apparatus according to claim 1 in which the optical passage is a solid transparent body whose exterior surface is made inwardly reflective.

8. Apparatus according to claim 1 in which the said individual sections are flat.

9. Apparatus according to claim 1 in which the said individual sections have a curvature opposite to that of the light conducting rod.

10. Apparatus according to claim 1 in which the number of said individual sections lies in the range 6 to 18.

11. Apparatus according to claim 10 in which the number of said individual sections is 12.

12. Apparatus according to claim 9 in which the curvature of the individual sections is a radius lying in the range ½ to ¼ of the radius of curvature of the light conducting rod.

* * * * *